July 25, 1933. E. C. HOWARD Plant Pat. 71
STRAWBERRY PLANT
Original Filed July 1, 1931
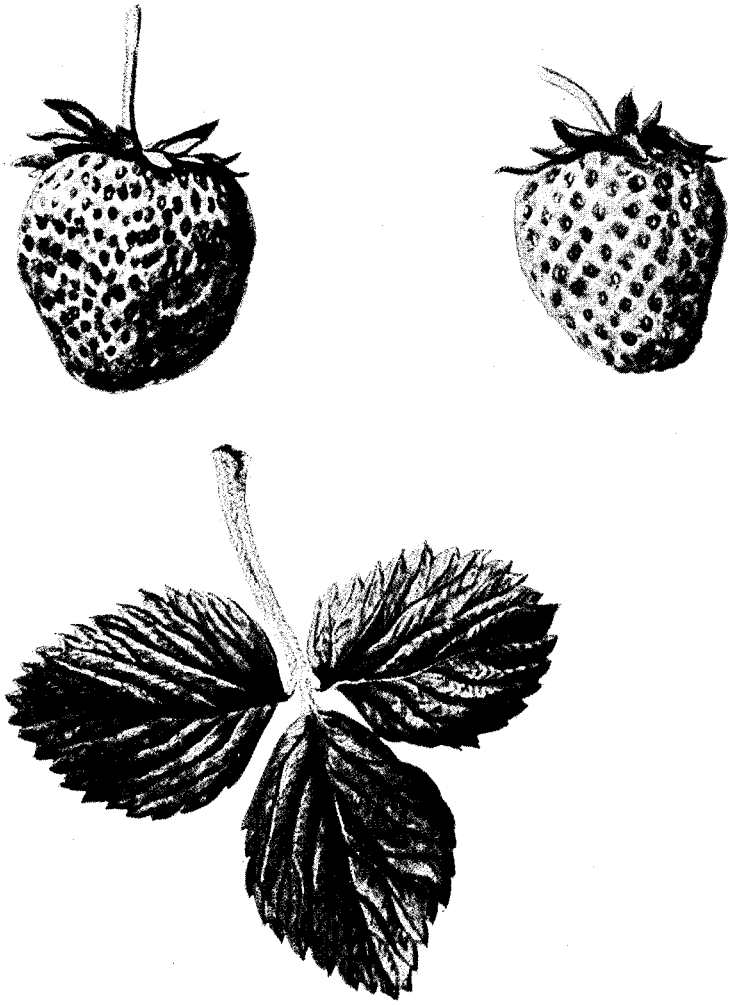
INVENTOR
Everett C. Howard
By Orville M Kile
PLANT·PATENT·AGENT Patented July 25, 1933

Plant Pat. 71

UNITED STATES PATENT OFFICE

EVERETT C. HOWARD, OF BELCHERTOWN, MASSACHUSETTS

STRAWBERRY PLANT

Refiled for abandoned application filed July 1, 1931, Serial No. 548,227. Divided and this application filed December 27, 1932. Serial No. 649,056.

My invention relates to improvements in commercial strawberry varieties. The present application is a substitute for the abandoned application filed July 1, 1931, Serial Number 548,227. The object of my invention is to provide a variety of strawberry suitable for commercial use, having a stronger root system and better fruit stems, and producing fruit of superior quality, as well as having other characteristics that make it superior to other existing varieties.

My new variety of strawberry plant is the result of definite scientific plant breeding reaching back over a period of many years. I made the final cross pollination which produced this new variety in 1907. This consisted of applying the pollen from a variety known as Howard 17 to the mother plant, Howard No. 103. I planted these seeds in the spring of 1908 and in 1909 found the present superior variety among the seedlings produced. This new variety was the most striking and distinct among the 1000 or more seedlings grown in the test beds at that time and resulting from 10 different crosses.

The mother plant—the Howard No. 103—was a seedling of the Crescent crossed by the Marshall, a berry famous for size, beauty and fine flavor.

The pollen parent—the Howard No. 17, now known as the Premier—was also a seedling of the Crescent crossed by another one of the Howard seedlings—the No. 1. The Howard No. 17, or Premier, is one of the best known of the newer commercial strawberry varieties.

After several years of testing and observing this new variety under conditions existing at Belchertown, Massachusetts, I undertook the usual long-term testing process used by conscientious originators of new varieties of small fruits and entered into arrangements with several of the leading State Agricultural Experiment Stations, to test out this variety under climatic, soil and other conditions to be found in these several States. In all cases, however, it was stipulated that these plants were sent out solely for testing purposes. They were neither sold to the experiment stations nor did they in turn sell any plants to others.

Introduction and sale to the public took place shortly after January 1, 1931, when plants of this variety were first offered for sale and described in a catalog issued by E. W. Townsend & Sons of Salisbury, Maryland.

The accompanying illustrations show in detail a leaf and several typical berries, two in full mature color, as borne by this variety of strawberry plant.

The following is a detailed description of its principal features and characters.

*Plant.*—Of medium to large size, very healthy and vigorous, producing good stocky runners freely, but not so freely as to produce undersized plants. The root system is especially notable, producing an exceedingly large number of long roots which branch and re-branch into a thick mat of root hairs. This characteristic makes for notable drouth resistance and heavy fruiting. The crown is wide and strong.

*Leaves.*—Bright green in color, ordinarily free from leaf spot and borne on upright stems, medium in size and having deeply notched edges, usually about 25 to each leaf heavily veined, leaf stems covered with hairs.

*Calyx.*—Usually consists of a single layer or row of sepals.

*Flowers.*—Are "imperfect" (pistillate) and the flower or fruit stems are strong and have the quality of standing rather erect or upright, thus tending to keep the fruit free of sand or dirt.

*Berries.*—Conic-wedge shaped, quite regular, large to very large in size; the color of the ripe berry is dark crimson, very attractive in appearance; the seeds are very slightly sunken and varying in color from yellowish on the shaded side of the berry to a dull dark red on the sunny side of the berry. The dark red color of the berry extends entirely through same. The flavor of the berry is sweet to sub-acid, sprightly and classed as very good. The flesh is meaty and in firmness ranks well above the average commercial variety, thus adding greatly to its value for shipping and general market use as well as for canning.

*Productivity.*—Exceedingly productive, surpassing Howard's Premier in this respect. The fruiting season is long, beginning with the medium early varieties and continuing to fruit with the late varieties.

Some of the more important features which I believe clearly distinguish my new variety of strawberry plant from all other varieties are:

1. Has a remarkably large and vigorous root system and withstands drouths better than most varieties.

2. Has well shaped berries of dark red color and the color goes all the way through the berry.

3. Its berries are larger, firmer and have a more sprightly flavor than other varieties including the Premier or Howard 17. This gives improved shipping and canning qualities.

4. More productive than most other varieties including Premier.

5. Fruit stems are stronger and more erect than those of most other varieties including Premier.

6. Has "imperfect" flowers.

Having thus described and disclosed my invention, I claim:

The variety of strawberry plant herein described, characterized particularly by its bright, vigorous and attractive foilage, its unusually heavy root system, its heavy production of berries of superior size, shape and color as shown, the dark red color extending all the way through the berry, and its firmness of flesh and sprightly flavor resulting in superior shipping and canning qualities.

EVERETT C. HOWARD.